(12) United States Patent
Choi et al.

(10) Patent No.: US 8,003,221 B2
(45) Date of Patent: Aug. 23, 2011

(54) METALLOCENYL DENDRIMER, ORGANIC MEMORY DEVICE USING THE SAME AND FABRICATION METHOD OF THE ORGANIC MEMORY DEVICE

(75) Inventors: Tae Lim Choi, Yongin-si (KR); Kwang Hee Lee, Yongin-si (KR); Sang Kyun Lee, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1099 days.

(21) Appl. No.: 11/715,941

(22) Filed: Mar. 9, 2007

(65) Prior Publication Data

US 2008/0111124 A1     May 15, 2008

(30) Foreign Application Priority Data

Nov. 13, 2006   (KR) .................. 10-2006-0111785

(51) Int. Cl.
*B32B 15/04*    (2006.01)
*B32B 9/04*    (2006.01)
*H01L 51/00*    (2006.01)

(52) U.S. Cl. ........ 428/469; 428/457; 428/688; 428/689; 428/702; 428/704; 257/40; 427/58

(58) Field of Classification Search .............. None
See application file for complete search history.

(56) References Cited

U.S. PATENT DOCUMENTS

| | | | | |
|---|---|---|---|---|
| 7,026,702 B2* | 4/2006 | Krieger et al. | ................ | 257/464 |
| 7,042,755 B1* | 5/2006 | Bocian et al. | ................ | 365/151 |
| 7,045,367 B2* | 5/2006 | Kaganove et al. | ........... | 436/532 |
| 7,537,842 B2* | 5/2009 | Burn et al. | .................... | 428/690 |
| 2005/0164029 A1* | 7/2005 | Burn et al. | .................... | 428/690 |

FOREIGN PATENT DOCUMENTS

WO     WO 2005092906 A1 * 10/2005

OTHER PUBLICATIONS

Thomas et al, Star-shaped polyferrocenes based on thiophene and triphenylamine: synthesis, spectroscopy and electrochemistry, Journal of Organic Chemistry 637-639, 2001, pp. 139-144.*
Casado et al, Redox-active ferrocenyl dendrimers and polymers in solution and immobilised on electrode surfaces, Coordination Chemistry Reviews 185-186, 1999, pp. 53-79.*

* cited by examiner

*Primary Examiner* — Monique R Jackson
(74) *Attorney, Agent, or Firm* — Harness, Dickey & Pierce, P.L.C.

(57) ABSTRACT

Disclosed are a metallocenyl dendrimer, an organic memory device using the metallocenyl dendrimer and a method for fabricating the organic memory device. The metallocenyl dendrimer may be composed of a dendrimer and metallocenes as redox species linked to the dendrimer. The organic memory device may possess the advantages of shorter switching time, decreased operating voltage, decreased fabrication costs and increased reliability. Based on these advantages, the organic memory device may be used as a highly integrated, large-capacity memory device.

16 Claims, 5 Drawing Sheets

METALLOCENYL DENDRIMER, ORGANIC MEMORY DEVICE USING THE SAME AND FABRICATION METHOD OF THE ORGANIC MEMORY DEVICE

PRIORITY STATEMENT

This non-provisional application claims priority under 35 U.S.C. §119 to Korean Patent Application No. 10-2006-0111785, filed on Nov. 13, 2006, in the Korean Intellectual Property Office (KIPO), the entire contents of which are herein incorporated by reference.

BACKGROUND

1. Field

Example embodiments relate to a metallocenyl dendrimer, an organic memory device using the metallocenyl dendrimer and a method for fabricating the organic memory device. Other example embodiments relate to a metallocenyl dendrimer composed of a dendrimer and metallocenes as redox species linked to the dendrimer, an organic memory device fabricated using the metallocenyl dendrimer with improved operating characteristics and improved non-volatility, and a method for fabricating the organic memory device.

2. Description of the Related Art

With the recent dramatic developments in digital communication technology, demand for a variety of memory devices has been increasing rapidly. Memory devices suitable for use in applications including, for example, portable computers and electronic devices, including mobile terminals, smart cards, electronic money, digital cameras, personal digital assistants, digital audio players and/or multimedia players, are required for retaining data in memory even when no power is being applied to the memory device, thereby tending to reduce the memory-related power consumption of the device. Conventional memory devices may include a bistable element that may be switched between a higher resistance state and a lower resistance state when a voltage is applied to the devices. Resistive memory devices are memories whose resistance is varied depending on an applied voltage and in which data is stored in response to variations in the resistance.

Chalcogenide materials, semiconductors and various types of oxides and nitrides are known to have resistive memory properties. Some organic materials are also found to have resistive memory properties. Of these resistive memory devices, organic memory devices may include an upper electrode, a lower electrode and a memory layer between the upper and lower electrodes, wherein the memory layer may be formed of an organic material and memory properties are realized by using bistability of resistance values obtained when a voltage is applied between the upper and lower electrodes. Next-generation organic memory devices ensure non-volatility, which is an advantage of conventional flash memories, and at the same time, overcome the disadvantages of undesirable processability, increased fabrication costs and decreased degree of integration.

For example, the related art discloses an organic memory device using 7,7,8,8-tetracyano-p-quinodimethane (CuTCNQ), which is an organometallic charge transfer complex compound. The related art also introduces a semiconductor device comprising an upper electrode, a lower electrode and an intermediate layer between the upper and lower electrodes wherein the intermediate layer is formed of a mixture of an ionic salt, e.g., NaCl or CsCl, and a conductive polymer.

The related art also suggests an organic memory device comprising organic active layers and a metal nanocluster applied between the organic active layers. However, this device has problems in that the yield of the device may be relatively low, the metal nanocluster may not be readily formed and the device may be reset at about 0 V, which may make the device actually unsuitable for use as a nonvolatile organic memory.

On the other hand, metallocenes and their derivatives are currently being investigated for their inherent electrical, optical and magnetic properties, for example, their ability to be oxidized to form mixed valent states. However, a major portion of research on metallocenes and their derivatives has been devoted to their use as fuel additives and polymerization catalysts. There hasn't been any research on the use of metallocenes and their derivatives as materials for active layers of organic memory devices.

SUMMARY

Therefore, example embodiments are provided below for addressing certain of the deficiencies and/or limitations of the related art, and example embodiments provide a metallocenyl dendrimer that may be used as a material for an organic active layer of an organic memory device to improve the operating characteristics of the organic memory device. Example embodiments provide an organic memory device comprising a metallocenyl dendrimer that possesses the advantages of shorter switching time, decreased operating voltage, decreased fabrication costs and increased reliability.

Example embodiments provide a method for fabricating an organic memory device by which an organic memory device may be fabricated by a simplified procedure at reduced costs and processed at a decreased temperature so that it may be applied to the manufacture of flexible memory devices.

In accordance with example embodiments, there is provided a metallocenyl dendrimer represented by Formula 1:

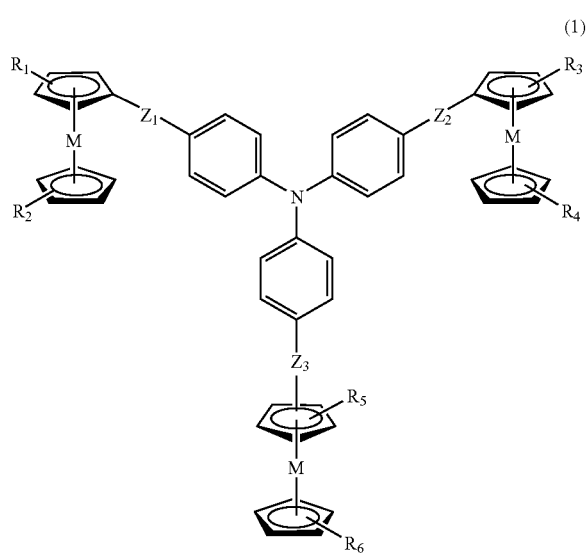

(1)

wherein $R_1$, $R_2$, $R_3$, $R_4$, $R_5$ and $R_6$, which may be identical to or different from each other, are independently H, a $C_1$-$C_{20}$ alkyl group, a $C_1$-$C_{20}$ alkoxy group, a $C_3$-$C_{20}$ cycloalkyl group, a $C_3$-$C_{20}$ heterocycloalkyl group, a $C_5$-$C_{30}$ aryl group, a $C_5$-$C_{30}$ heteroaryl group, a $C_7$-$C_{30}$ arylalkyl group, or a $C_5$-$C_{30}$ aryloxy group; $Z_1$, $Z_2$ and $Z_3$, which may be identical to or different from each other, are independently a single bond, —C≡C—, —(CH$_2$)$_n$— (in which n is from about 1 to about 20), or a carbonyl group; and M is Fe, Ru, Zr or Ti.

The metallocenyl dendrimer of Formula 1 may be one represented by Formula 2 or 3:

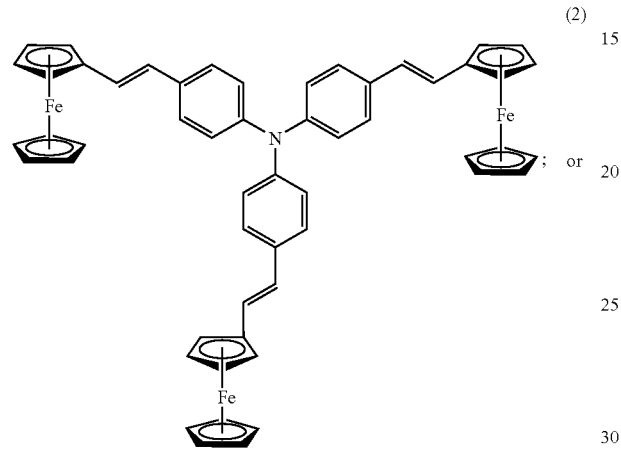

(2)

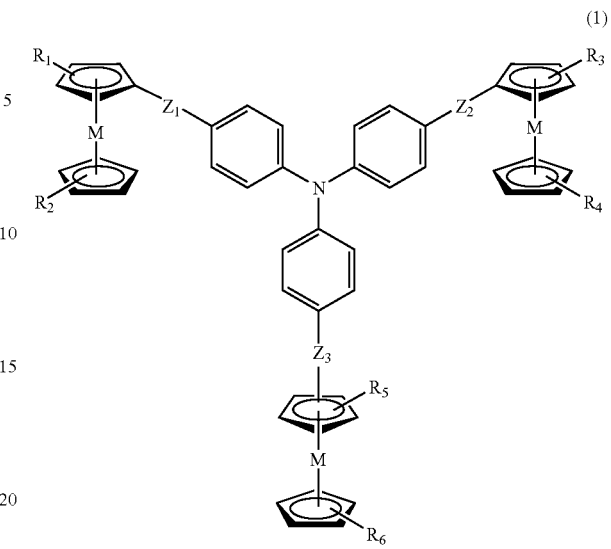

(1)

wherein $R_1$, $R_2$, $R_3$, $R_4$, $R_5$ and $R_6$, which may be identical to or different from each other, are independently H, a $C_1$-$C_{20}$ alkyl group, a $C_1$-$C_{20}$ alkoxy group, a $C_3$-$C_{20}$ cycloalkyl group, a $C_3$-$C_{20}$ heterocycloalkyl group, a $C_5$-$C_{30}$ aryl group, a $C_5$-$C_{30}$ heteroaryl group, a $C_7$-$C_{30}$ arylalkyl group, or a $C_5$-$C_{30}$ aryloxy group; $Z_1$, $Z_2$ and $Z_3$, which may be identical to or different from each other, are independently a single bond, —C≡C—, —(CH$_2$)$_n$— (in which n is from about 1 to about 20), or a carbonyl group; and M is Fe, Ru, Zr or Ti.

In accordance with example embodiments, there is provided a method for fabricating a memory device comprising a first electrode, a second electrode and an organic active layer between the first and second electrodes, wherein the method comprises forming the organic active layer using a metallocenyl dendrimer of Formula 1:

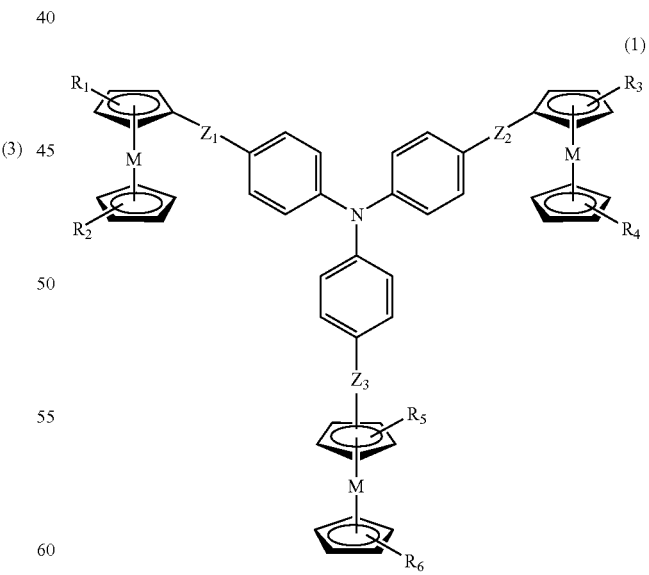

(1)

In accordance with example embodiments, there is provided an organic memory device comprising a first electrode, a second electrode and an organic active layer between the first and second electrodes, wherein the organic active layer is formed of a metallocenyl dendrimer of Formula 1:

wherein $R_1$, $R_2$, $R_3$, $R_4$, $R_5$ and $R_6$, which may be identical to or different from each other, are independently H, a $C_1$-$C_{20}$ alkyl group, a $C_1$-$C_{20}$ alkoxy group, a $C_3$-$C_{20}$ cycloalkyl group, a $C_3$-$C_{20}$ heterocycloalkyl group, a $C_5$-$C_{30}$ aryl group, a $C_5$-$C_{30}$ heteroaryl group, a $C_7$-$C_{30}$ arylalkyl group, or a $C_5$-$C_{30}$ aryloxy group; $Z_1$, $Z_2$ and $Z_3$, which may be identical to or different from each other, are independently a single bond, —C≡C—, —$(CH_2)_n$ (in which n is from about 1 to about 20), or a carbonyl group; and M is Fe, Ru, Zr or Ti.

BRIEF DESCRIPTION OF THE DRAWINGS

Example embodiments will be more clearly understood from the following detailed description taken in conjunction with the accompanying drawings.

FIG. 1 is a schematic cross-sectional view of an organic memory device according to example embodiments;

FIG. 2 is a schematic perspective view of a memory matrix employing a memory device according to example embodiments;

FIG. 3 is a $^1$H-NMR spectrum of a metallocenyl dendrimer prepared in Preparative Example 1;

FIG. 4 is a $^1$H-NMR spectrum of a metallocenyl dendrimer prepared in Preparative Example 2;

FIG. 5 is a graph showing variations in the current of an organic memory device fabricated in Example 1 in response to a voltage applied to the device; and FIG. 6 is a graph showing variations in resistance ratio (on/off ratio) of an organic memory device fabricated in Example 1.

Figure 1:
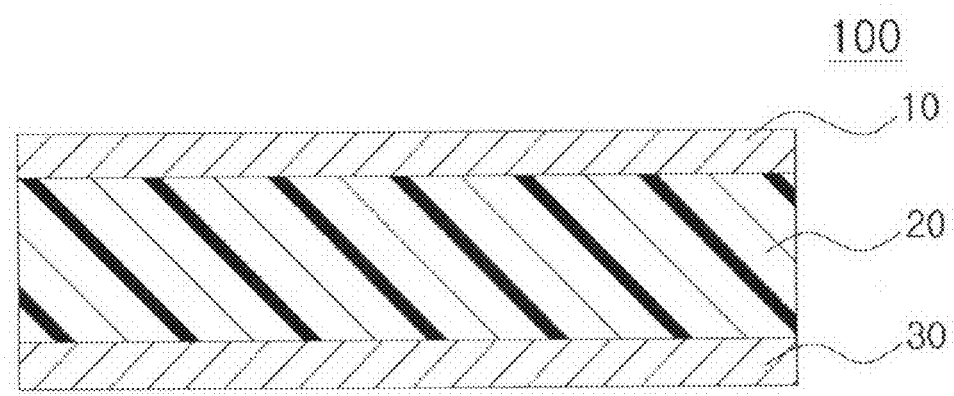
FIGS. 1-6 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. In particular, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Example embodiments will now be described in greater detail with reference to the accompanying drawings. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Dendrimers are regularly repeated tree-like or radially branched compounds. Dendrimers are three-dimensional spherical molecules consisting of a central core and chains that radiate from the central core. The growth stages of branches in dendrimers are represented as "generations" and proceed stepwise to form shells on a central core for each generation.

Example embodiments are directed to a metallocenyl dendrimer represented by Formula 1:

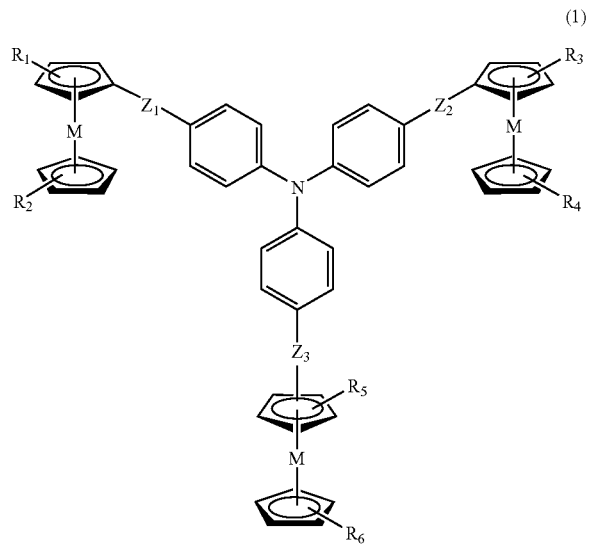

(1)

wherein $R_1$, $R_2$, $R_3$, $R_4$, $R_5$ and $R_6$, which may be identical to or different from each other, are independently H, a $C_1$-$C_{20}$ alkyl group, a $C_1$-$C_{20}$ alkoxy group, a $C_3$-$C_{20}$ cycloalkyl group, a $C_3$-$C_{20}$ heterocycloalkyl group, a $C_5$-$C_{30}$ aryl group, a $C_5$-$C_{30}$ heteroaryl group, a $C_7$-$C_{30}$ arylalkyl group, or a $C_5$-$C_{30}$ aryloxy group; $Z_1$, $Z_2$ and $Z_3$, which may be identical to or different from each other, are independently a single bond, —C=C—, —(CH$_2$)$_n$ (in which n is from about 1 to about 20), or a carbonyl group; and M is Fe, Ru, Zr or Ti.

As represented in Formula 1, the metallocenyl dendrimer of example embodiments may be a low-molecular weight material in which metallocenes having multiple oxidation states are linked to a conjugated dendrimer. The metallocenyl dendrimer of example embodiments may realize bistable memory properties due to reversible redox reactions of the metallocenyl groups. Because the metallocenyl dendrimer has a low molecular weight and is soluble, it may be used to form various layers (e.g., organic active layers) of organic memory devices by solution processes (e.g., spin coating). The metallocenyl dendrimer of example embodiments may have a molecular weight of about 500 to about 10,000.

The aromatic rings of the metallocenes of the metallocenyl dendrimer according to example embodiments may have one or more substituents (e.g. $R_1$ to $R_6$). The substituents $R_1$ to $R_6$ may be identical to or different from each other, and non-limiting examples thereof include H, $C_1$-$C_{20}$ alkyl groups, $C_1$-$C_{20}$ alkoxy groups, $C_3$-$C_{20}$ cycloalkyl groups, $C_3$-$C_{20}$ heterocycloalkyl groups, $C_5$-$C_{30}$ aryl groups, $C_5$-$C_{30}$ heteroaryl groups, $C_7$-$C_{30}$ arylalkyl groups and $C_5$-$C_{30}$ aryloxy groups.

The alkyl may be a straight-chained or branched group, and specific examples thereof include methyl, ethyl, propyl, isobutyl, sec-butyl, tert-butyl, pentyl, iso-amyl and hexyl.

The alkoxy is a functional group formed by eliminating a proton from a hydroxyl group of an alcohol. The alkoxy group is represented by —OR wherein R is a monovalent hydrocarbon group selected from $C_1$-$C_{20}$ alkyl, alkenyl, aryl and arylalkyl groups.

The term "cycloalkyl" as used herein refers to a $C_3$-$C_{30}$ monovalent monocyclic system. At least one hydrogen atom contained in the cycloalkyl group may be substituted.

The term "heterocycloalkyl" as used herein refers to a $C_3$-$C_{20}$ monovalent monocyclic system consisting of one to three heteroatoms selected from N, O, P and S atoms and the remaining ring carbon atoms. At least one hydrogen atom contained in the heterocycloalkyl group may be substituted.

The term "aryl" as used herein refers to a carbocyclic aromatic system including one or more aromatic rings in which the rings may be attached together in a pendent manner or may be fused. Specific examples of the aryl group include aromatic groups, e.g., phenyl, naphthyl, and tetrahydronaphthyl. At least one hydrogen atom contained in the aryl group may be substituted.

The term "heteroaryl" as used herein refers to a $C_5$-$C_{30}$ cyclic aromatic system consisting of one to three heteroatoms selected from N, O, P and S atoms and the remaining ring carbon atoms in which the rings may be attached together in a pendant manner or may be fused. At least one hydrogen atom contained in the heteroaryl group may be substituted.

The term "arylalkyl" as used herein refers to a group in which a part of hydrogen atoms contained in the aryl group defined above are substituted with lower alkyl radicals, e.g., methyl, ethyl and propyl. Examples of the arylalkyl group include benzyl and phenylethyl. At least one hydrogen atom contained in the arylalkyl group may be substituted.

The aryloxy includes about 5 to about 30 carbon atoms. Specific examples of the aryloxy group include phenyloxy, naphthyloxy and anthryloxy.

Metallocenyl dendrimers that may be represented by Formula 1 may include those of Formulae 2 and 3:

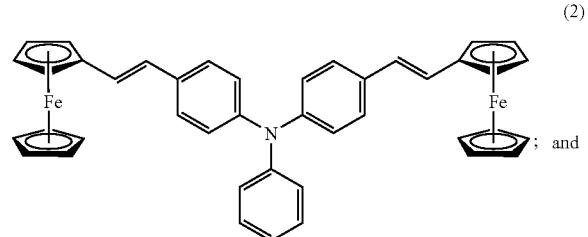

(2)

; and

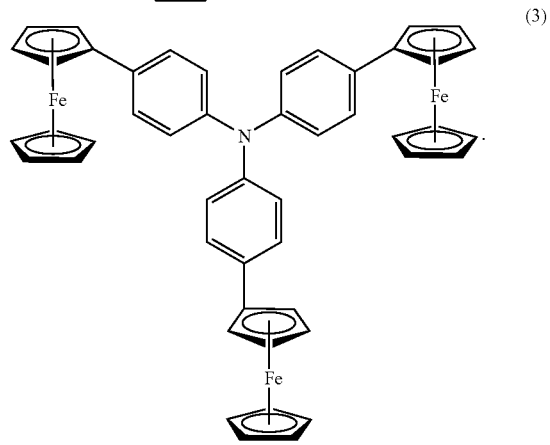

(3)

Unlike polymers, dendrimers may be synthesized through accurate prediction of molecular design parameters, e.g., molecular weight and topology. In addition, dendrimers possess the advantage that the physical properties of the final products may be predicted. Macromolecules, e.g., polymers, are commonly prepared through the degradation or conversion of functional groups, while dendrimers are synthesized by a multi-stage synthesis in which two or three chemical reactions are repeatedly carried out. The multi-stage synthesis may allow dendrimers to have the number of surface functional groups as initially calculated. Various types of chemical techniques are currently employed to synthesize dendrimers. Highly applicable synthetic techniques may be widely used.

A dendrimer may be prepared by selecting a compound for forming branched terminals, a compound acting as a monomer for forming a tree-like structure, and a compound for forming a central core. The metallocenyl dendrimer of example embodiments may be synthesized by a divergent strategy, a convergent strategy or a combination thereof using a triiodophenyl amine as a chemical species for forming a central core.

For example, as depicted in Reaction 1, the triiodophenyl amine may be reacted with vinylferrocene by Heck coupling to give the metallocenyl dendrimer of Formula 2 according to example embodiments. A palladium-catalyzed C—C coupling may be formed between the triiodophenyl amine as an aryl halide and the vinylferrocene as an alkene in the presence of a base. The C—C bond formed by Heck coupling is a double bond whose major stereochemistry is a trans structure.

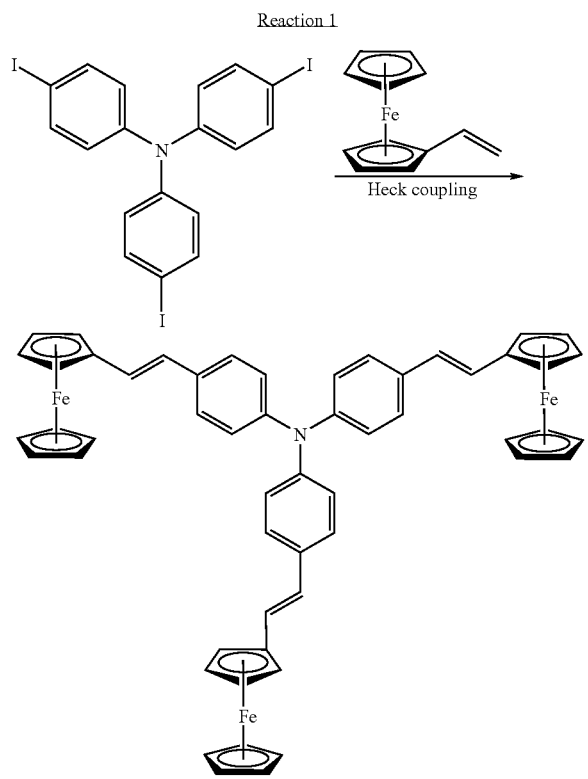

On the other hand, as depicted in Reaction 2, ferrocene boronic acid may be reacted with the triiodophenyl amine by Suzuki coupling in the presence of a catalyst to give the metallocenyl dendrimer of Formula 3. Specifically, the organoboronic acid may be reacted with the haloaryl compound in the presence of a palladium catalyst by Suzuki coupling to induce linking of the ferrocene to the triiodophenyl amine.

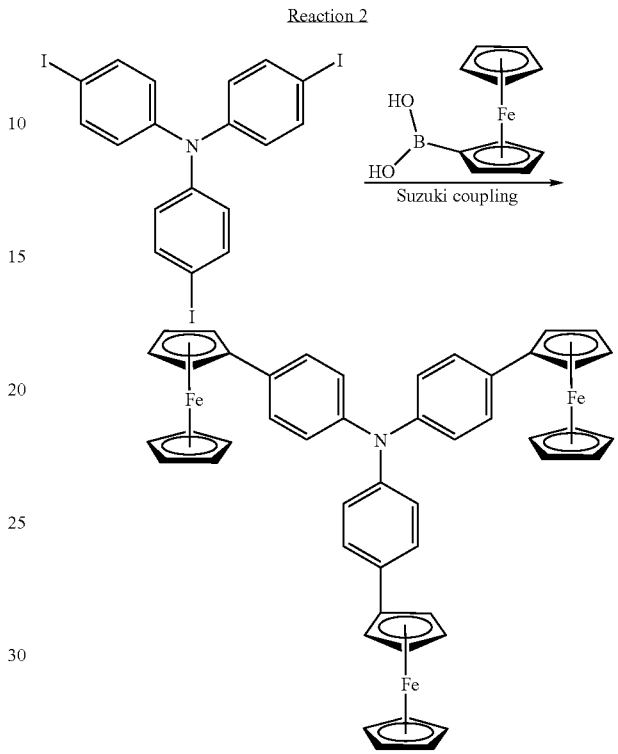

The dendrimer may be used to prepare a bulkier molecule by a convergent or divergent strategy. For example, a triiodophenyl amine may be bonded to styrenyl-3,5-dicarboxylaldehyde by Heck coupling. Then, the resulting aldehyde may be converted to an alkene compound by Wittig reaction. The alkene compound may be reacted with bromoferrocene by Heck coupling to synthesize a bulkier dendrimer.

Example embodiments are directed to an organic memory device comprising a first electrode, a second electrode and an organic active layer between the first and second electrodes, wherein the organic active layer may be formed of the metallocenyl dendrimer of Formula 1.

FIG. 1 is a schematic cross-sectional view of an organic memory device according to example embodiments. With reference to FIG. 1, the organic memory device 100 of example embodiments may include a first electrode 10, a second electrode 30 and an organic active layer 20 between the first and second electrodes. The resistance values of the organic active layer 20 obtained when a voltage is applied to the memory device 100 may show bistability, and as a result, memory properties of the memory device may be achieved.

The organic active layer 20 of the organic memory device may provide increased conductivity and bistability. The metallocenyl dendrimer of example embodiments may be a conjugated polymer and may have electron or hole conductivity due to its conjugated structure. The conductivity of the organic active layer may be varied depending on the redox state of the metallocenes conjugated to the backbone of the conjugated dendrimer of the metallocenyl dendrimer according to example embodiments, and as a result, bistability of the organic active layer may be achieved. For example, when a voltage is applied to the organic memory device, the metallocenes of the metallocenyl dendrimer constituting the organic active layer may lose or gain one or more electrons to cause a variation in oxidation state. The oxidation state of the organic active layer formed of the metallocenyl dendrimer may be maintained until another voltage is applied to the organic active layer. Further, the oxidation state may be maintained even when no power is being applied to the memory device, thus ensuring non-volatility of the organic memory device according to example embodiments.

The conjugation of the triphenylamine moiety and the ferrocenes present in the metallocenyl dendrimer of example embodiments may allow intramolecular charge transfer, and hopping may induce intermolecular charge transfer. On the other hand, a ferrocene compound may be stable and may exhibit inherent conductivity when it is in the $Fe^{2+}$ state. A voltage greater than a threshold voltage or light energy having a particular wavelength may be applied to a ferrocene compound in the $Fe^{2+}$ state to excite the ferrocene compound to the oxidized state (e.g. $Fe^{3+}$ (ferrocenium)). The ferrocene compound in the oxidized state may exhibit improved charge transfer capacity and improved conductivity, compared to the ferrocene compound in the $Fe^{2+}$ state. Accordingly, oxidation-reduction states of the ferrocenes of the metallocenyl dendrimer may be factors determining two resistance states of the organic memory device according to example embodiments.

When a proper electrical voltage is applied between the two electrodes of the memory device according to example embodiments, the organic active layer may switch between a higher resistance state and a lower resistance state depending on the oxidation-reduction states of the ferrocenes of the metallocenyl dendrimer. Assuming that the lower resistance state is defined as data "1" and the higher resistance state is defined as data "0", two logic states of the data may be stored. When the metallocenyl dendrimer of example embodiments has two or more oxidation states, two or more logic states may be stored.

The organic active layer of the organic memory device according to example embodiments may be formed by combining the metallocenyl dendrimer with a conductive polymer selected from polythiophene, polyvinylcarbazole, polyaniline, polypyrrole, polyphenylenevinylene, polyfluorene and polyacetylene. Specific examples of such conductive polymers may include poly(3-hexylthiophene-2,5-diyl), poly (9-vinylcarbazole), polyaniline (emeraldine base), poly[2-methoxy-5-(2-ethylhexyloxy)-1,4-phenylenevinylene], and poly(9,9-didodecylfluorenyl-2,7-yleneethynylene).

Figure 2:
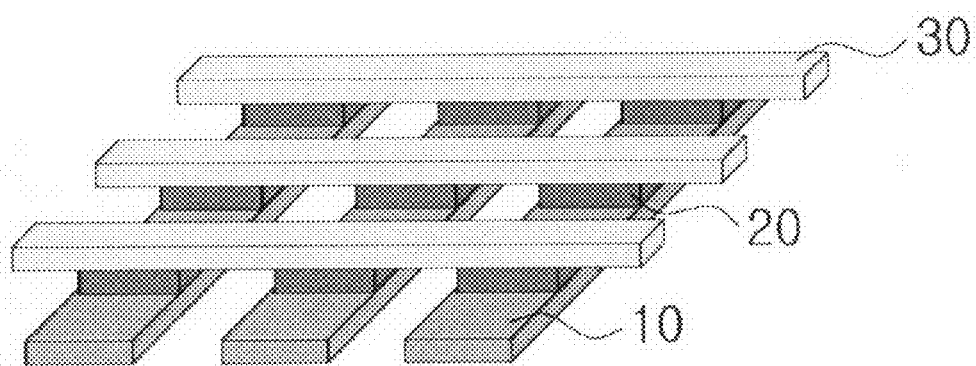

FIG. 2 is a schematic perspective view of an exemplary memory matrix employing the memory device of example embodiments. As shown in FIG. 2, the memory matrix may be formed on a suitable substrate. An organic active layer 20 may be formed between the first and second electrodes 10 and 30. With this configuration of the memory matrix, a plurality of memory cells may be formed at intersections between first electrodes 10 and second electrodes 30. The memory cells may provide bistability characteristics.

The organic memory device of example embodiments may be fabricated on a substrate. As the substrate, a common organic or inorganic substrate may be used, for example, a flexible substrate. Examples of suitable materials for the substrate may include, but may not be limited to, glass, silicon, surface-modified glass, polypropylene, activated acrylamide ceramics, membranes, gels, and aerogels.

The first electrode 10 and the second electrode 30 may be made of at least one electrically conductive material selected from the group consisting of metals, metal alloys, metal nitrides, metal oxides, metal sulfides, conductive polymers, organic conductors, nanostructures, and crystals. Specific examples of materials for the first and second electrodes may include, but may not be limited to, gold (Au), silver (Ag), platinum (Pt), copper (Cu), cobalt, nickel, tin, titanium (Ti), tungsten (W), aluminum (Al), and indium tin oxide (ITO).

The organic memory device of example embodiments may further include a barrier layer formed under the first electrode or on the second electrode to prevent or reduce damage to the first or second electrode due to attacks by the organic materials. The barrier layer may be formed of a material selected from the group consisting of LiF, $SiO_x$, $AlO_x$, $NbO_x$, $TiO_x$, $CrO_x$, $VO_x$, $TaO_x$, $CuO_x$, $MgO_x$, $WO_x$ and $AlNO_x$, and may be formed of a material selected from the group consisting of $SiO_2$, $Al_2O_3$, $Cu_2O$, $TiO_2$ and $V_2O_3$. The barrier layer may also be formed of an organic material, e.g., Alq3, polymethylmethacrylate, polystyrene and/or PET. The barrier layer may have a thickness of about 20 Å to about 300 Å.

The organic memory device of example embodiments may be well suited for use in computers, portable information devices, cell phones, medical devices, radar devices and/or satellite devices. Because the organic memory device of example embodiments may be reduced in size and weight, the portability of portable digital devices, including cell phones, PDAs, notebook computers, digital cameras, portable multimedia players and/or DMB terminals may be improved.

Example embodiments are directed to a method for fabricating an organic memory device using the metallocenyl dendrimer. An organic memory device fabricated by the method of example embodiments may include a first electrode, a second electrode and an organic active layer between the first and second electrodes, wherein the organic active layer is formed of the metallocenyl dendrimer of Formula 1. Materials for a substrate, the electrodes and the organic active layer are the same as those explained above.

Coating processes for the formation of the organic active layer using the metallocenyl dendrimer may not be particularly limited, and examples thereof may include spin coating, spray coating, electrostatic coating, dip coating, blade coating, roll coating, and ink-jet printing. The organic active layer may have a thickness of about 50 Å to about 3,000 Å.

Any solvent that may dissolve the metallocenyl dendrimer may be used for spin coating. At least one solvent selected from the group consisting of chloroform, N-methylpyrrolidone, acetone, cyclopentanone, cyclohexanone, methyl ethyl ketone, ethyl cellosolve acetate, butylacetate, ethylene glycol, toluene, xylene, tetrahydrofuran, dimethylformamide, chlorobenzene, acetonitrile and mixtures thereof may be used to form the organic active layer by spin coating. A solvent system or solvent mixture of two or more of these solvents in any miscible ratio may also be used.

Baking may be performed after the coating. Baking processes may be suitably selected according to the solvent used. Taking into consideration the boiling point of the coating solvent used, the baking may be performed on a hot plate for about 10 minutes or more. The first and second electrodes may be formed by known coating processes, including deposition (e.g., thermal evaporation), sputtering, e-beam evaporation and/or spin coating.

Hereinafter, example embodiments will be explained in more detail with reference to the following examples. However, these examples are given for the purpose of illustration and are not to be construed as limiting the scope of example embodiments.

EXAMPLES

Preparative Example 1

Figure 3:
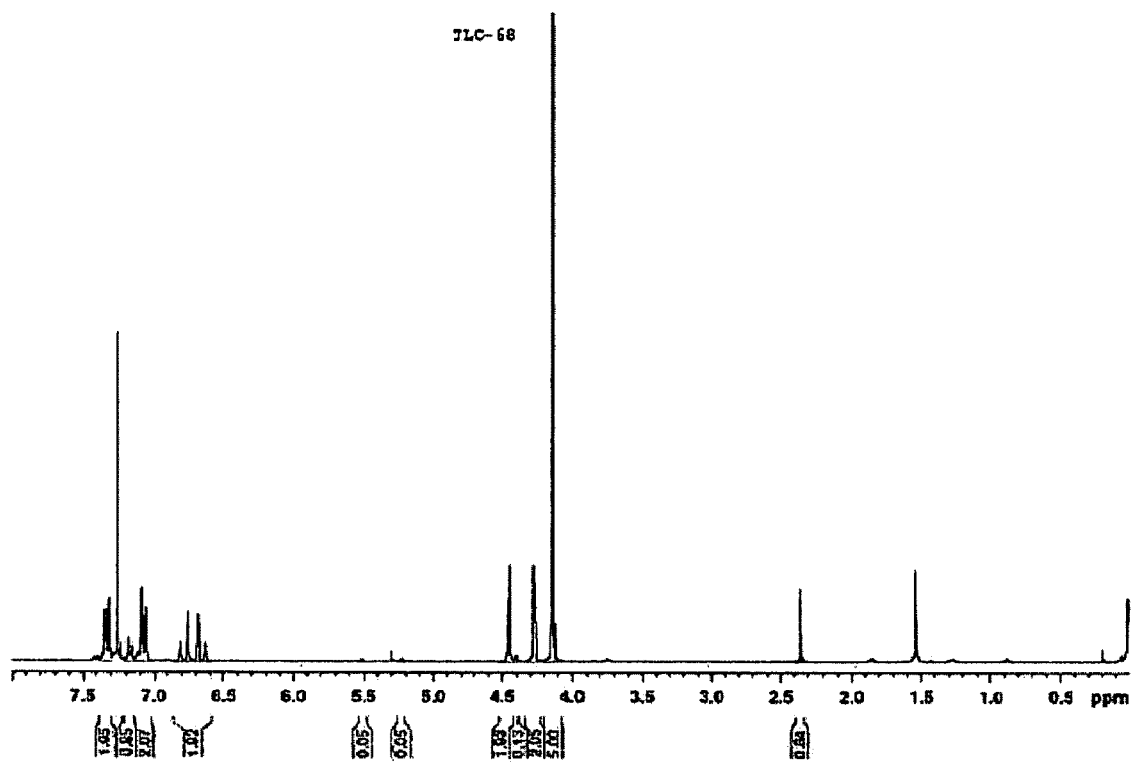

About 424 mg (about 2 mmol) of vinylferrocene, about 312 mg (about 0.5 mmol) of tris(4-iodophenyl)amine and about 7 mg (about 6 mol %) of palladium acetate were placed in a flask. After a reflux condenser was connected to the flask, about 3 ml of 1,4-dioxene as a solvent, about 480 µl (about 2 mmol) of tri-n-butylamine as a base and about 11 µl (about 9 mol %) of tri-t-butylphosphine were injected into the flask using a syringe under a nitrogen atmosphere. The solution was degassed with nitrogen gas, and refluxed in an oil bath. The reaction was allowed to proceed for about 4 days. The reaction solution was diluted with about 10 ml of methylene chloride and neutralized with a saturated aqueous solution of ammonium chloride. The neutralized solution was transferred to a separatory funnel, followed by phase separation. The obtained organic layer was dried over anhydrous magnesium sulfate and passed through a glass filter to obtain a transparent polymer solution. The polymer solution was evaporated under reduced pressure to remove the solvents. The residue was purified by column chromatography using toluene/hexane (½), yielding the metallocenyl dendrimer (about 301 mg) of Formula 2 as an orange solid. The $^1$H-NMR spectrum of the metallocenyl dendrimer is shown in FIG. 3.

Preparative Example 2

Figure 4:
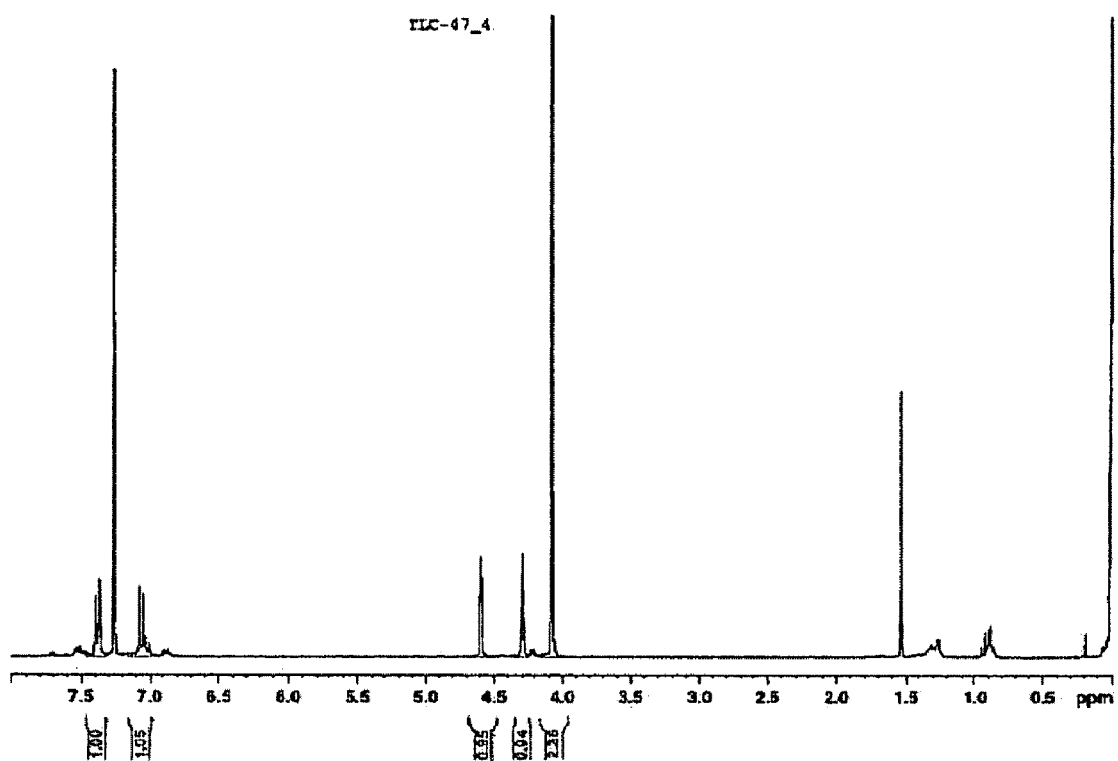

About 690 mg (about 3 mmol) of ferrocene boronic acid, about 310 mg (about 0.5 mmol) of tris(4-iodophenyl)amine and about 40 mg (about 10 mol %) of Pd(dppf)Cl$_2$ were placed in a flask. After a reflux condenser was connected to the flask, about 6 ml of toluene as a solvent and about 5 ml (about 1.33 M) of tetraethylammonium hydroxide as a base were injected into the flask using a syringe under a nitrogen atmosphere. The solution was degassed with nitrogen gas, and refluxed in an oil bath. The reaction was allowed to proceed for about 4 days. The reaction solution was diluted with about 20 ml of methylene chloride and neutralized with a saturated aqueous solution of ammonium chloride. The neutralized solution was transferred to a separatory funnel, followed by phase separation. The obtained organic layer was dried over anhydrous magnesium sulfate and passed through a glass filter to obtain a transparent polymer solution. The polymer solution was evaporated under reduced pressure to remove the solvents. The residue was purified by column chromatography using toluene/hexane (½), yielding the metallocenyl dendrimer (about 130 mg) of Formula 3 as an orange solid. The $^1$H-NMR spectrum of the metallocenyl dendrimer is shown in FIG. 4.

Example 1

ITO was deposited on a glass substrate (Corning 1737) having a size about 5 cm×about 5 cm and patterned by photolithography/wet etching. The patterned substrate was dipped in acetone/isopropyl alcohol, ultrasonicated for about 15 minutes, and dried. About 10 mg of the metallocenyl dendrimer prepared in Preparative Example 1 was dissolved in about 1 ml of chlorobenzene (C$_6$H$_5$Cl) by sonication for about 30 minutes. The solution was passed through a syringe filter (pore size: about 0.2 µm) made of PTFE, and spin-coated at about 2,000 rpm on the ITO/glass substrate for about 30 seconds. The remaining solvent was removed by baking the coated substrate on a hot plate at about 110° C. for about 10 minutes to form an organic active layer. The organic active layer thus formed had a thickness of about 50 nm to about 100 nm, as measured using an Alpha-Step™ profilometer. A shadow mask was placed on the resulting substrate and introduced into a thermal evaporator. LiF was deposited to a thickness of about 5 nm on the organic active layer to form a barrier layer, and thereafter, Al was deposited to a thickness of about 80 nm on the barrier layer by thermal evaporation to form an upper electrode, completing fabrication of an organic memory device according to example embodiments. The thicknesses of the electrodes were controlled using a quartz crystal monitor.

Test Example 1

Test for Switching Characteristics of Memory Device

Figure 5:
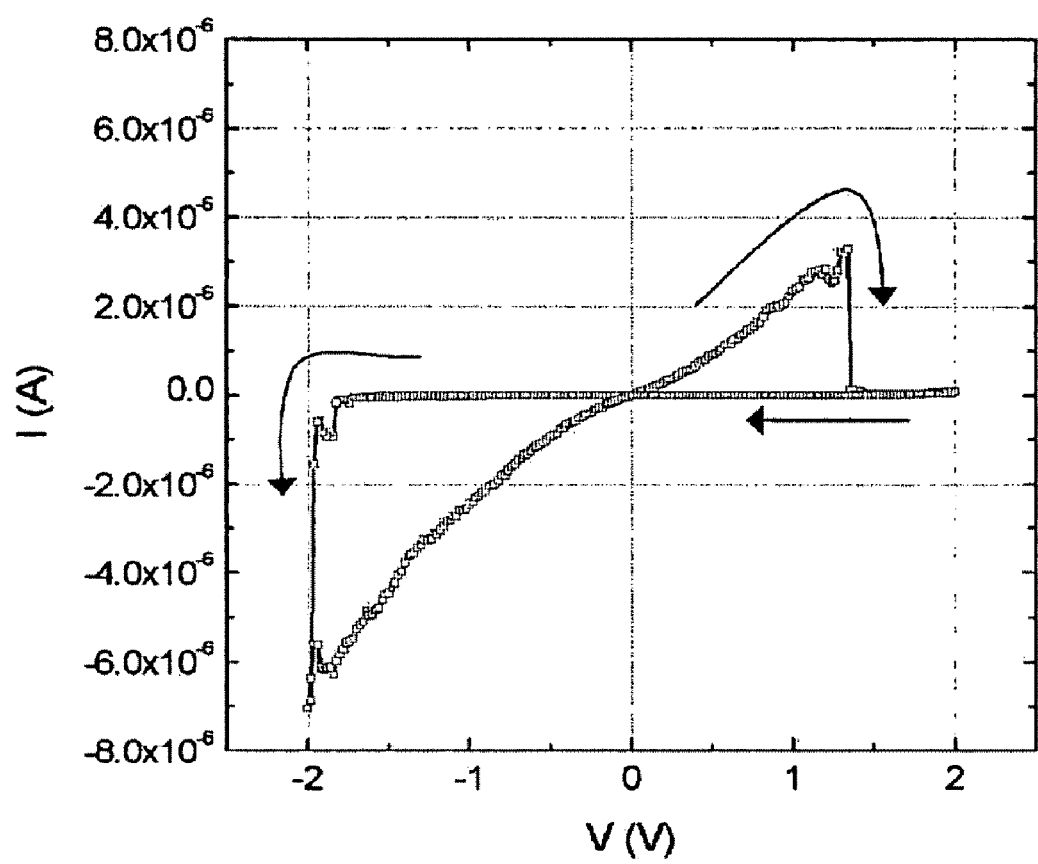
Figure 6:
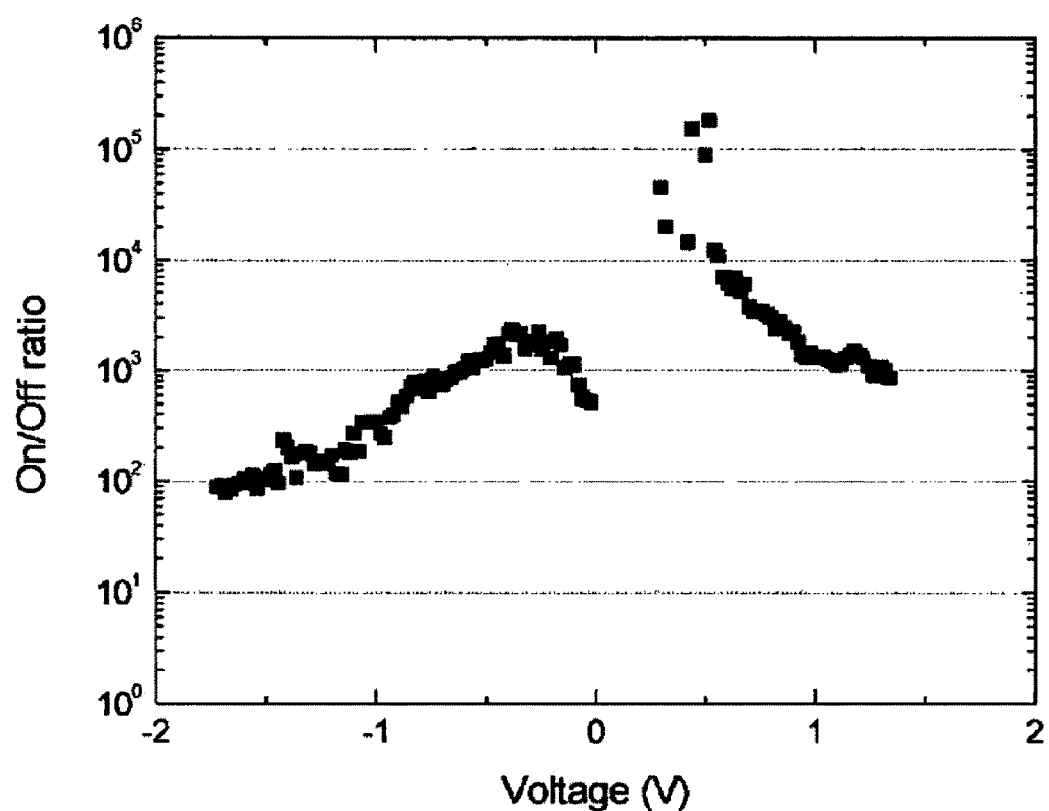

The electrical properties of the memory device fabricated in Example 1 were evaluated using a Keithley S4200 semiconductor characterization system. After a voltage was applied to the memory device, the switching properties of the memory device were evaluated as variations in current and the obtained results are shown in FIG. 5. The resistance ratio (on/off ratio) of the organic memory device was measured in two different resistance states, and the results are shown in FIG. 6.

Referring to FIG. 5, the memory device showed two conducting states when a maximum or increased voltage of about 2 V was swept in both positive (+) and negative (−) directions. Where sweeping was carried out by the application of a positive voltage, the memory device became a higher resistance state (e.g. an "OFF" state) at about 1.4 V. Where a negative bias voltage was applied, the memory device was switched into a lower resistance state (e.g. an "ON" state) at about −2 V. When a voltage was continuously applied in the sweep mode of both directions, the memory device was continuously switched with a variation in switching voltage of about 0.3 V. Each of the two different resistance states could be maintained for a relatively long period of time even when no voltage or current was applied to the memory device. The graph of FIG. 6 shows that the resistance ratio of the memory device in both resistance states was measured to be a minimum of about $10^2$, indicating that the memory device is suitable for practical application.

Although example embodiments have been disclosed for illustrative purposes, those skilled in the art will appreciate that various modifications and variations are possible, without departing from the scope and spirit of the appended claims. Accordingly, such modifications and variations are intended to come within the scope of the claims.

As apparent from the above description, the organic memory device of example embodiments may offer the advantages of possible miniaturization, shorter switching time, decreased operating voltage, decreased fabrication costs and increased reliability over inorganic memory devices. Based on these advantages, the organic memory device of example embodiments may be used as a lightweight, highly integrated, large-capacity memory device.

In addition, because the organic memory device of example embodiments may be fabricated by a simpler and economical process, e.g., spin coating, and may be processed at a decreased temperature, it may be applied to a flexible memory device.

Furthermore, the organic memory device fabricated using the metallocenyl dendrimer of example embodiments may achieve improved nonvolatile memory characteristics, compared to organic memory devices fabricated using conventional conductive polymers.

What is claimed is:

1. An organic memory device comprising a first electrode, a second electrode and an organic active layer between the first and second electrodes, wherein the organic active layer is formed of a metallocenyl dendrimer represented by Formula 1:

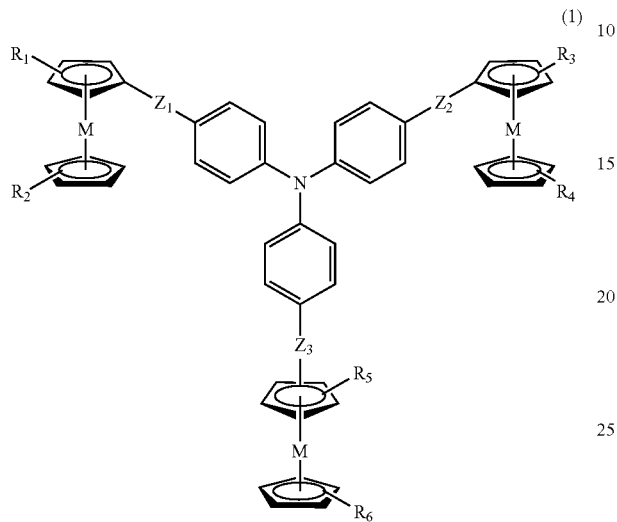

wherein $R_1$, $R_2$, $R_3$, $R_4$, $R_5$ and $R_6$, which is identical to or different from each other, are independently H, a $C_1$-$C_{20}$ alkyl group, a $C_1$-$C_{20}$ alkoxy group, a $C_3$-$C_{20}$ cycloalkyl group, a $C_3$-$C_{20}$ heterocycloalkyl group, a $C_5$-$C_{30}$ aryl group, a $C_5$-$C_{30}$ heteroaryl group, a $C_7$-$C_{30}$ arylalkyl group, or a $C_5$-$C_{30}$ aryloxy group; $Z_1$, $Z_2$ and $Z_3$, which is identical to or different from each other, are independently a single bond, —C═C—, —(CH$_2$)$_n$— in which n is from about 1 to about 20 or a carbonyl group; and M is Fe, Ru, Zr or Ti.

2. The organic memory device according to claim 1, wherein the metallocenyl dendrimer is the compound represented by Formula 2 or 3:

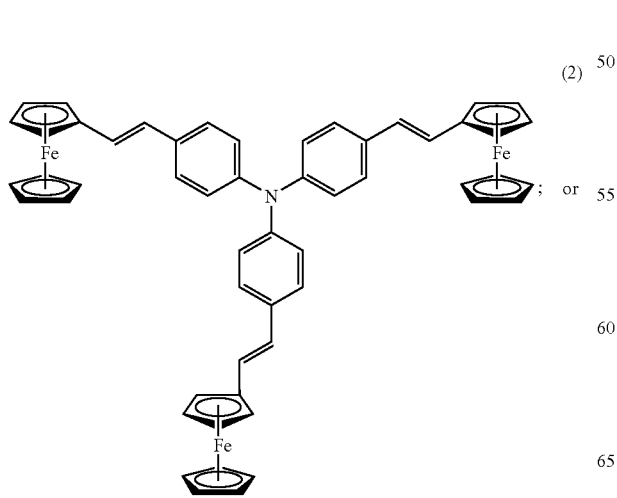

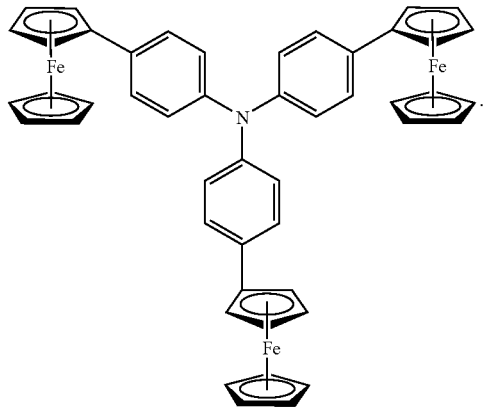

3. The organic memory device according to claim 1, wherein the first or second electrode is made of at least one material selected from the group consisting of metals, metal alloys, metal nitrides, metal oxides, metal sulfides, organic conductors, nanostructures, and crystals.

4. The organic memory device according to claim 3, wherein the first or second electrode is made of at least one material selected from the group consisting of gold (Au), silver (Ag), platinum (Pt), copper (Cu), cobalt, nickel, tin, titanium (Ti), tungsten (W), aluminum (Al), and indium tin oxide (ITO).

5. The organic memory device according to claim 1, further comprising:
a barrier layer formed under the first electrode or on the second electrode.

6. The organic memory device according to claim 5, wherein the barrier layer is formed of an inorganic material selected from the group consisting of $SiO_x$, $AlO_x$, $NbO_x$, $TiO_x$, $CrO_x$, $VO_x$, $TaO_x$, $CuO_x$, $MgO_x$, $WO_x$ and $AlNO_x$, or an organic material selected from the group consisting of Alq3, polymethylmethacrylate, polystyrene and PET.

7. The organic memory device according to claim 6, wherein the barrier layer is formed of a material selected from the group consisting of $SiO_2$, $Al_2O_3$, $Cu_2O$, $TiO_2$, and $V_2O_3$.

8. A method for fabricating a memory device comprising a first electrode, a second electrode and an organic active layer between the first and second electrodes, wherein the method includes forming the organic active layer using a metallocenyl dendrimer of Formula 1:

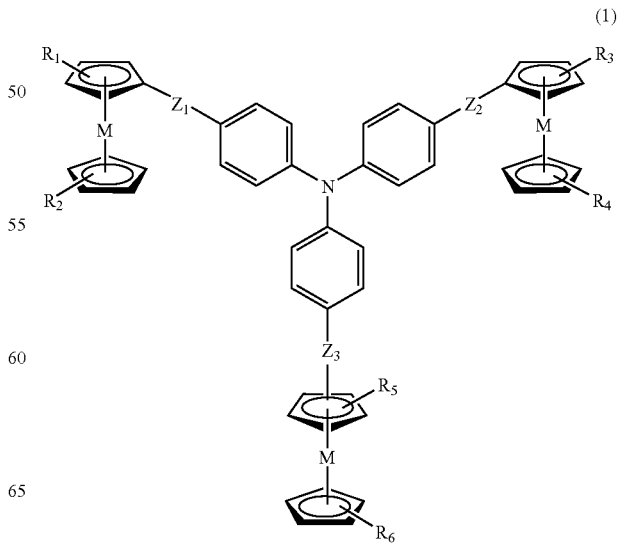

wherein $R_1$, $R_2$, $R_3$, $R_4$, $R_5$ and $R_6$, which is identical to or different from each other, are independently H, a $C_1$-$C_{20}$ alkyl group, a $C_1$-$C_{20}$ alkoxy group, a $C_3$-$C_{20}$ cycloalkyl group, a $C_3$-$C_{20}$ heterocycloalkyl group, a $C_5$-$C_{30}$ aryl group, a $C_5$-$C_{30}$ heteroaryl group, a $C_7$-$C_{30}$ arylalkyl group, or a $C_5$-$C_{30}$ aryloxy group; $Z_1$, $Z_2$ and $Z_3$, which is identical to or different from each other, are independently a single bond, —C≡C—, —(CH$_2$)$_n$— in which n is from about 1 to about 20, or a carbonyl group; and M is Fe, Ru, Zr or Ti.

9. The method according to claim 8, wherein the metallocenyl dendrimer is the compound represented by Formula 2 or 3:

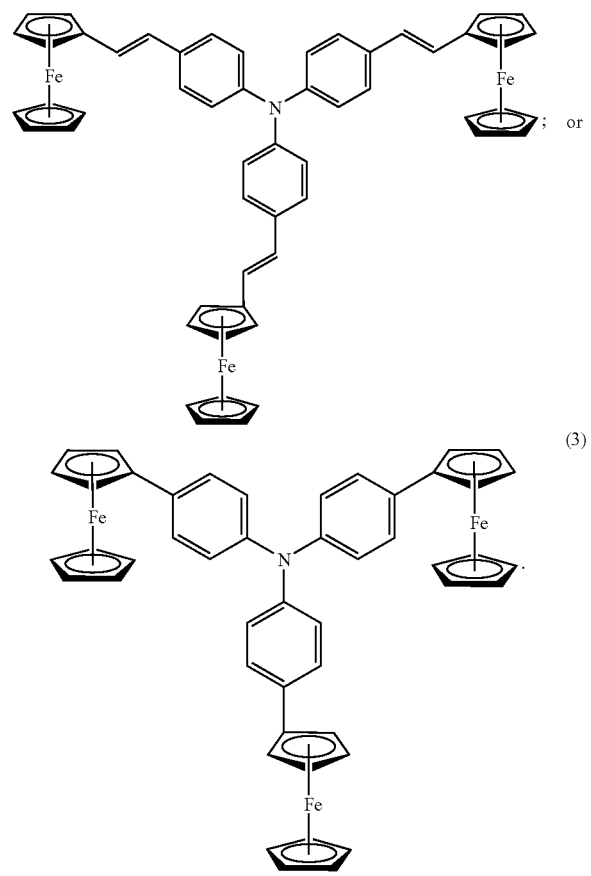

10. The method according to claim 8, wherein the organic active layer is formed by coating the metallocenyl dendrimer by a coating process selected from the group consisting of spin coating, spray coating, electrostatic coating, dip coating, blade coating, and roll coating.

11. The method according to claim 8, wherein the metallocenyl dendrimer is coated using at least one solvent selected from the group consisting of chloroform, N-methylpyrrolidone, acetone, cyclopentanone, cyclohexanone, methyl ethyl ketone, ethyl cellosolve acetate, butyl acetate, ethylene glycol, toluene, xylene, tetrahydrofuran, dimethylformamide, chlorobenzene, and acetonitrile.

12. The method according to claim 8, wherein the first or second electrode is made of at least one material selected from the group consisting of metals, metal alloys, metal nitrides, metal oxides, metal sulfides, organic conductors, nanostructures, and crystals.

13. The method according to claim 12, wherein the first or second electrode is made of at least one material selected from the group consisting of gold (Au), silver (Ag), platinum (Pt), copper (Cu), cobalt, nickel, tin, titanium (Ti), tungsten (W), aluminum (Al), and indium tin oxide (ITO).

14. The method according to claim 8, further comprising:
forming a barrier layer under the first electrode or on the second electrode of the memory device.

15. The method according to claim 14, wherein the barrier layer is formed of an inorganic material selected from the group consisting of $SiO_x$, $AlO_x$, $NbO_x$, $TiO_x$, $CrO_x$, $VO_x$, $TaO_x$, $CuO_x$, $MgO_x$, $WO_x$ and $AlNO_x$, or an organic material selected from the group consisting of Alq3, polymethylmethacrylate, polystyrene and PET.

16. The method according to claim 15, wherein the barrier layer is formed of a material selected from the group consisting of $SiO_2$, $Al_2O_3$, $Cu_2O$, $TiO_2$, and $V_2O_3$.

* * * * *